(12) United States Patent
Cates et al.

(10) Patent No.: US 7,169,395 B1
(45) Date of Patent: Jan. 30, 2007

(54) MULTIVALENT IMMUNOGENIC COMPOSITION CONTAINING RSV SUBUNIT COMPOSITION AND INFLUENZA VIRUS PREPARATION

(75) Inventors: George A. Cates, Richmond Hill (CA); Suryaprakash Sambhara, Markham (CA); David Burt, Ajax (CA); Michel H. Klein, Toronto (CA)

(73) Assignee: Sanofi Pasteur Limited, Toronto (CA)

( * ) Notice: Subject to any disclaimer, the term of this patent is extended or adjusted under 35 U.S.C. 154(b) by 0 days.

(21) Appl. No.: 09/868,177

(22) PCT Filed: Dec. 16, 1999

(86) PCT No.: PCT/CA99/01194

§ 371 (c)(1),
(2), (4) Date: Nov. 23, 2001

(87) PCT Pub. No.: WO00/35481

PCT Pub. Date: Jun. 22, 2000

Related U.S. Application Data (63) Continuation-in-part of application No. 09/213,770, filed on Dec. 17, 1998.

(51) Int. Cl.
*A61K 39/00* (2006.01)
*A61K 39/12* (2006.01)
*A61K 39/145* (2006.01)
*A61K 39/155* (2006.01)
*A61K 45/00* (2006.01)

(52) U.S. Cl. .............. 424/202.1; 424/184.1; 424/204.1; 424/206.1; 424/211.1; 424/278.1; 530/300; 530/350

(58) Field of Classification Search ......... 424/211.1, 424/202.1, 204.1, 206.1, 209.1, 210.1, 186.1, 424/199.1, 237.1, 184.1, 193.1, 278.1; 514/2, 514/8; 436/516; 536/23.72, 24.2; 435/5, 435/235.1, 236, 69.1, 69.3, 320.1; 530/300, 530/350, 361, 388.3, 395
See application file for complete search history.

(56) References Cited

U.S. PATENT DOCUMENTS

| | | | |
|---|---|---|---|
| 5,494,673 A | 2/1996 | Andrianov et al. | |
| 5,612,037 A | 3/1997 | Huebner et al. | |
| 5,762,939 A * | 6/1998 | Smith et al. | 424/210.1 |
| 5,824,536 A * | 10/1998 | Webster et al. | 435/235.1 |
| 5,911,998 A | 6/1999 | Potash et al. | |
| 6,020,182 A | 2/2000 | Cates et al. | |
| 6,022,726 A * | 2/2000 | Palese et al. | 435/236 |
| 6,309,649 B1 * | 10/2001 | Cates et al. | 424/211.1 |
| 2002/0136739 A1 * | 9/2002 | Cates et al. | 424/211.1 |

FOREIGN PATENT DOCUMENTS

| | | |
|---|---|---|
| WO | WO 95/02628 | 1/1995 |
| WO | WO 95/34308 | 12/1995 |
| WO | WO 95/34323 | 12/1995 |
| WO | WO 96/33738 | 10/1996 |
| WO | WO 98/02457 | 1/1998 |

OTHER PUBLICATIONS

Groothuis et al., "Safety and Immunogenicity of a Purified F Protein Respiratory Syncytial Virus (PFP-2) Vaccine in Seropositive Children with Bronchopulmanary Dysplasia," Journal of Infectious Diseases, vol. 177(2), pp. 467-469 (1998).*
Falsey et al., ., "Safety and Immunogenicity of a Purified F Protein Respiratory Syncytial Virus (PFP-2) Vaccine in Ambulatory Adults over Age 60," Vaccine, vol. 14(13), pp. 1214-1218 (1996).*
Crowe, Vaccine, vol. 13, pp. 415-421 (1995).*
Hall et al., "Immunity to and Frequency of Reinfection with Respiratory Syncytial Virus," J. Infect. Dis., vol. 163, pp. 693-698 (1991).*
Tang et al., Journal of Virology, vol. 77 No. 20, pp. 10819-10828 (Oct. 2003).*
Prince et al., Journal of Virology, vol. 74 No. 22, pp. 10287-10292 (Nov. 2000).*
Dudas et al., Clinical Microbiology Reviews, vol. 11 No. 3, pp. 430-439 (Jul. 1998).*
Mlinaric-Galinovic G, Falsey AR, Walsh EE, 1996. Respiratory syncytial virus infection in the elderly. Eur J Clin Microbiol Infect Dis 1996.
Collins, P., McIntosh, K., and Chanock, R.M. in "Fields Virology" ed. by Fields, B.N., Knipe, D.M., and Howley, P.M., Lippincott-Raven Press, New York, (1996) pp. 1313-1351.

(Continued)

*Primary Examiner*—Bruce R. Campell
*Assistant Examiner*—Zachariah Lucas
(74) *Attorney, Agent, or Firm*—Michael I. Stewart; Sim & McBurney (57) ABSTRACT

Immunogenic compositions for administration to adults, particularly to the elderly, to protect them against disease caused by infection by respiratory syncytial virus and by influenza virus comprise an immunoeffective amount of a mixture of purified fusion (F) protein, attachment (G) protein and matrix (M) protein of RSV and an immunoeffective amount of a non-virulent influenza virus preparation. The components of the composition, when formulated as a vaccine for in vivo administration, do not impair the immunogenicity of each other. The immunogenic composition may also contain an adjuvant.

13 Claims, 5 Drawing Sheets

OTHER PUBLICATIONS

Walsh, E.E., Hall, C.B., Briselli, M., Brandiss, M.W. and Schlesinger, J.J. (1987) J. Infect. Dis. 155, 1198-1204.
Walsh, E.E., Hruska, J. (1983) J. Virol. 47, 171-177.
Levine, S., Kleiber-France, R., and Paradiso, P.R. (1987) J. Gen. Virol. 69, 2521-2524.
Anderson, L.J. Hierholzer, J.C., Tsou, C., Hendry, R.M., Fernie, B.F., Stone, Y. and McIntosh, K. (1985), J. Infect. Dis. 151, 626-633.
Johnson, P.R., Olmsted, R.A., Prince, G.A., Murphy, B.R., Alling, D.W., Walsh, E.E. and Collins, P.L. (1987) J. Virol. 61 (10), 3163-3166.
Cherrie, A.H., Anderson, K., Wertz, G.W., and Openshaw, P.J.M. (1992) J. Virology 66, 2102-2110.
Kim, H.W., Canchola, J.G., Brandt, C.D., Pyles, G., Chanock, R.M. Jensen, K., and Parrott, R.H. (1969) Amer. J. Epidemiology 89, 422-434.
Friedewald, W.T., Forsyth, B.R., Smith, C.B., Gharpure, M.S., and Chanock, R.M. (1968) JAMA 204, 142-146.
Walsh, E.E., Brandriss, M.W., Schlesinger, J.J. (1985) J. Gen. Virol. 66, 409-415.
Walsh, E.E., Schlesinger, J.J. and Brandriss, M.W. (1984) J. Gen. Virol. 65, 761-766.
Routledge, E.G., Wilcocks, M.M., Samson, A.C.R., Morgan, L., Scott, R., Anderson, J.J., and Toms, G.L. (1988) J. Gen. Virology 69, 293-303.
Fulginiti, V.A., Eller, J.J., Sieber, O.F., Joyner, I.W., Minamitani, M. and Meiklejohn, G. (1969) Am J.Epidemiol. 89 (4), 435-448.
Chin, J., Magoffin, R.L., Shearer, L.A., Schieble, J. H. and Lennette, E.H. (1969) Am. J. Epidemiol. 89 (4), 449-463.
Kapikian, A.Z., Mitchell, R.H., Chanock, R.M., Shvedoff, R.A. and Stewart, C.E. (1969) Am. J.Epidemiol. 89 (4),405-421.
Kim, H.W., Arrobio, J.O., Pyles, G., Brandt, C.D. Camargo, E., Chanock, R.M. and Parrott, R.H. (1971) Pediatrics 48, 745-755.
Wright, P.F., Belshe, R.B., Kim, H.W., Van Voris, L.P. and Chanock, r.M. (1982) Infect. Immun. 37 (1), 397-400.
Wright, P.F., Chinozaki, T. and Fleet, W. (1976) J. Pediatr. 88, 931-936.
Belshe, R.B., Van Voris, P. and Mufson, M.A. (1982) J. Infect. Dis. 145, 311-319.
Murphy, B.R, Prince, G.A., Walsh, E.E., Kim, H.W., Parrott, R.H., Hemming V.G., Rodriguez, W.J., and Chanock, R.M.. J. Clin. Microbiol. (1986), 24(2), 197-202.
Connors, M., Collins, P.L., Firestone, C.Y., Sotnikov, A.V., Waitze, A., Davis, A.R., Hung, P.P., Chanock, R.M., Murphy, b. (1992) Vaccine, 10, 475-484.
Prince, G.A., Jenson, A.B., Hemming, V.G., Murphy, E.R., Walsh, E.E., Horswood, R.L. and Chanock, R.L. (1986b) J. Virol. 57 (3), 721-728.
Piedra, P.A., Camussi, F. and Ogra, P.L. (1989) J. Gen. Virol. 70, 325-333.
Payne G.L., et al. Vaccine vol. 16, pp. 92-98 1998.
Fattom Ali et al. Vaccine 17 (1999) pp. 126-133.
Ambrosch F. et al., Combined vaccination against yellow fever . . . Vaccine 1994 vol. 12; pp. 625-628.
Frey Sharon et al., The Journal of Infectious Diseases 1999; 180:2018-2022.
Insel. A. Richard., Potential alterations in Immnogenicity by Combining or Simultaneously Adminstering Vaccine Components. pp. 35-47.
Plotkin A.S. & Orenstein A.W. Vaccines Third Edition. pp. 508-530.
Glezen, W.P., Paredes, A. Allison, J.E., Taber, L.H. and Frank, A.L. (1981), J. Pediatr. 98, 708-715.
Chanock, R.M., Parrot, R.H., Connors, M. Collins, P.L. and Murphy, B.R. (1992) Pediatrics 90, 137-142.
Martin, A.J. Gardiner, P.S. and McQuillin, J. (1978). Lancel II, 1035-1038.
Robbins, A., and Freeman, P. (1988) Sci. Am. 259, 126-133.
Glezen, W.P., Taber, L.H., Frank, A.L. and Kasel, J.A. (1986) Am. J. Dis. Child. 140, 543-546.
Katz, S.L. New vaccine development establishing priorities. vol. 1. Washington: National Academic Press. (1985) pp. 397-409.
Wertz, G.W., Sultender, W.M. (1992) Biotech. 20, 151-176.
McIntosh, K. and Chanock, R.M. (1990) in Fields Virology (Fields, B.M., and Knipe, D.M. eds.) pp. 1045-1075, Raven Press, Ltd., New York.
Murray AR, Dowell SF, 1997. Respiratory syncytial virus: not just for kids. Hosp. Pract. (Off Ed) Jul. 15, 1997; 32(7): 87-8, 91-4.

* cited by examiner

MULTIVALENT IMMUNOGENIC COMPOSITION CONTAINING RSV SUBUNIT COMPOSITION AND INFLUENZA VIRUS PREPARATION This application is a national phase application under 35 U.S.C. 371 of PCT/CA99/01194 filed Dec. 16, 1999, which is a continuation-in-part of U.S. patent application Ser. No. 09/213,770 filed Dec. 17, 1998.

FIELD OF INVENTION

This invention relates to multivalent immunogenic composition, particularly for administration to adults.

BACKGROUND TO THE INVENTION

Human respiratory syncytial virus is the main cause of lower respiratory tract infections among infants and young children (refs. 1 to 3—a list of references appears at the end of the disclosure and each of the references in the list is incorporated herein by reference thereto). Globally, 65 million infections occur every year resulting in 160,000 deaths (ref. 4). In the USA alone, 100,000 children may require hospitalization for pneumonia and bronchiolitis caused by RS virus in a single year (refs. 5, 6). Providing inpatient and ambulatory care for children with RS virus infections costs in excess of $340 million annually in the USA (ref. 7). Severe lower respiratory tract disease due to RS virus infection predominantly occurs in infants two to six months of age (ref. 8). Approximately 4,000 infants in the USA die each year from complications arising from severe respiratory tract disease caused by infection with RS virus and parainfluenza type 3 virus (PIV-3). The World Health Organization (WHO) and the National Institute of Allergy and Infectious Disease (NIAID) vaccine advisory committees have ranked RS virus second only to HIV for vaccine development.

RSV infection in adults was initially considered a significant problem only in certain high-risk populations, such as the institutionalized elderly. However, evidence has been accumulating that the infection occurs frequently in previously healthy adults (ref. 9).

RSV infections in the elderly usually represent reinfections in those who have had many prior episodes. These infections have been reported to cause altered airway resistance and exacerbration of chronic obstructive lung disease.

In adults over 60 years old, RSV usually causes mild nasal congestion and may also result in fever, anorexia, pneumonia, brochitis and deaths (ref. 10).

The structure and composition of RSV has been elucidated and is described in detail in the textbook “Fields Virology”, Fields, B. N. et al. Raven Press, N.Y. (1996), in particular, Chapter 44, pp 1313–1351 “Respiratory Syncytial Virus” by Collins, P., McIntosh, K., and Chanock, R. M. (ref. 11).

The two major protective antigens of RSV are the envelope fusion (F) and attachment (G) glycoproteins (ref 12). The F protein is synthesized as an about 68 kDa precursor molecule ($F_0$) which is proteolytically cleaved into disulfide-linked $F_1$ (about 48 kDa) and $F_2$ (about 20 kDa) polypeptide fragments (ref. 13). The G protein (about 33 kDa) is heavily O-glycosylated giving rise to a glycoprotein of apparent molecular weight of about 90 kDa (ref. 14). Two broad subtypes of RS virus have been defined A and B (ref. 15). The major antigenic differences between these subtypes are found in the G glycoprotein while the F glycoprotein is more conserved (refs. 7, 16).

In addition to the antibody response generated by the F and G glycoproteins, human cytotoxic T cells produced by RSV infection have been shown to recognize the RSV F protein, matrix protein M, nucleoprotein N, small hydrophobic protein SH, and the nonstructural protein 1b (ref. 17).

A safe and effective RSV vaccine is not available and is urgently needed. Approaches to the development of RS virus vaccines have included inactivation of the virus with formalin (ref. 18), isolation of cold-adapted and/or temperature-sensitive mutant viruses (ref. 19) and purified F or G glycoproteins (refs. 20, 21, 22). Clinical trial results have shown that both live attenuated and formalin-inactivated vaccines failed to adequately protect vaccines against RS virus infection (refs. 23 to 25). Problems encountered with attenuated cold-adapted and/or temperature-sensitive RS virus mutants administered intranasally included clinical morbidity, genetic instability and overattenuation (refs. 26 to 28). A live RS virus vaccine administered subcutaneously also was not efficacious (ref. 29). Inactivated RS viral vaccines have typically been prepared using formaldehyde as the inactivating agent. Murphy et al. (ref. 30) have reported data on the immune response in infants and children immunized with formalin-inactivated RS virus. Infants (2 to 6 months of age) developed a high titre of antibodies to the F glycoprotein but had a poor response to the G protein. Older individuals (7 to 40 months of age) developed titres of F and G antibodies comparable to those in children who were infected with RS virus. However, both infants and children developed a lower level of neutralizing antibodies than did individuals of comparable age with natural RS virus infections. The unbalanced immune response, with high titres of antibodies to the main immunogenic RS virus proteins F (fusion) and G (attachment) proteins but a low neutralizing antibody titre, may be in part due to alterations of important epitopes in the F and G glycoproteins by the formalin treatment. Furthermore, some infants who received the formalin-inactivated RS virus vaccine developed a more serious lower respiratory tract disease following subsequent exposure to natural RS virus than did non-immunized individuals (refs. 24, 25). The formalin-inactivated RS virus vaccines, therefore, have been deemed unacceptable for human use.

Evidence of an aberrant immune response also was seen in cotton rats immunized with formalin-inactivated RS virus (ref. 31). Furthermore, evaluation of RS virus formalin-inactivated vaccine in cotton rats also showed that upon live virus challenge, immunized animals developed enhanced pulmonary histopathology (ref. 32).

The mechanism of disease potentiation caused by formalin-inactivated RS virus vaccine preparations remains to be defined but is a major obstacle in the development of an effective RS virus vaccine. The potentiation may be partly due to the action of formalin on the F and G glycoproteins. Additionally, a non-RS virus specific mechanism of disease potentiation has been suggested, in which an immunological response to contaminating cellular or serum components present in the vaccine preparation could contribute, in part, to the exacerbated disease (ref. 33). Indeed, mice and cotton rats vaccinated with a lysate of HEp-2 cells and challenged with RS virus grown on HEp-2 cells developed a heightened pulmonary inflammatory response.

Furthermore, RS virus glycoproteins purified by immunoaffinity chromatography using elution at acid pH were immunogenic and protective but also induced immunopotentiation in cotton rats (refs. 31, 34).

Influenza virus infection is one of the most common causes of respiratory tract diseases. Typically, the disease results in a high fever, usually 100° F. to 103° F. in adults, often higher in children, and respiratory symptoms, such as sore throat, running or stuffy nose, as well as headache, muscle aches and extreme fatigue. In a typical year, influenza is associated with about 20,000 deaths in the US, and many more hospitalizations (CDC).

Influenza viruses are divided into three types, designated A, B and C. Types A and B are responsible for epidemics that occur almost every winter. Influenza viruses continually change over time by mutation, which is termed antigenic drift.

Influenza A viruses are classified into sub-types on the basis of two surface antigens, hemagglutinin (H) and neuraminidase (N). Three subtypes of the hemagglutinin (H1, H2, H3) and two sub-types of neuraminidase (N1, N2) are recognized among influenza A viruses that have caused widespread human diseases. Immunity to these antigens reduces the likelihood of infections and lessens the severity of the disease if infection occurs.

As a result of antigenic drift, major epidemics of respiratory disease caused by new variants of influenza continue to occur. Thus, the antigenic characteristics of the circulating strains provide the basis for selecting the virus strains included in each year's vaccine.

Although there are many actual and potential benefits of vaccines that combine antigens to confer protection against multiple pathogens, these combinations may have a detrimental effect on the immunogenicity of the individual components.

As described above, RSV and influenza virus infections are prevalent in the adult population and particularly the elderly and it would be desirable to confer protection against such infection by the administration of a single vaccine composition. However, any potential detrimental effect of combining immunogens suitable for conferring protection against both RSV and influenza virus in a single formulation are unknown.

SUMMARY OF THE INVENTION

The inventors have surprisingly found that combining a mixture of RSV proteins with non-virulent influenza virus in a vaccine formulation provides an immune response which is substantially the same as the response obtained by administration of the components individually. Accordingly, there is no observed detrimental effect on the immunogenicity of the individual components by combining them in a single formulation. The inventors have also surprisingly found that, in the presence of the non-virulent influenza virus, an enhanced immune response to the mixture of RSV proteins can be obtained by formulating the immunogenic composition with an adjuvant.

Accordingly, in one aspect of the present invention, there is provided a multivalent immunogenic composition for conferring protection in a host against disease caused by infection by respiratory syncytial virus (RSV) and influenza virus, which comprises (a) an immunoeffective amount of a mixture of purified fusion (F) protein, attachment (G) protein and matrix (M) protein of RSV, and (b) an immunoeffective amount of a non-virulent influenza virus preparation. The immunogenic composition preferably is formulated as a vaccine for in vivo administration to the host, particularly an adult human host (at least 18 years of age), wherein the individual components (a) and (b) of the composition are formulated such that the immunogenicity of the individual components (a) and (b) is not impaired.

The immunogenic compositions of the invention may be formulated as microparticles, capsules, ISCOMs or liposomes. The immunogenic compositions may further comprise at least one other immunogenic or immunostimulating material, which may be at least one adjuvant or at least one immunomodulator, such as cytokines including IL-2.

The immunogenic composition provided herein may further comprise an adjuvant, particularly an adjuvant which imparts an enhanced immune response to RSV when compared to the RSV mixture formulated with the adjuvant in the absence of the non-virulent influenza virus preparation.

The at least one adjuvant may be selected from the group consisting of aluminum phosphate, aluminum hydroxide, QS21, Quil A or derivatives or components thereof, calcium phosphate, calcium hydroxide, zinc hydroxide, a glycolipid analog, an octodecyl ester of an amino acid, a muramyl dipeptide, polyphosphazene, ISCOPREP, a lipoprotein, ISCOM matrix, DC-Chol, DDBA, and other adjuvants and bacterial toxins, components and derivatives thereof as, for example, described in U.S. Ser. No. 08/258,228 filed Jun. 10, 1994, assigned to the assignee hereof and the disclosure of which is incorporated herein by reference thereto (WO 95/34323). Under particular circumstances, adjuvants that induce a Th1 response are desirable. Advantageous combinations of adjuvants are described in copending U.S. patent application Ser. No. 08/483,856 filed Jun. 7, 1995, assigned to the Assignee hereof and the disclosure of which is incorporated herein by reference (WO 95/34308).

Preferably, the adjuvant in the polyphosphazene, i.e. poly-di(carboxylatophenoxy)-phosphazene (PCPP).

The immunogenic composition of the invention may be formulated in single dosage form, wherein the mixture of RSV proteins is present in an amount of about 10 to about 200 μg, preferably about 50 to about 100 μg, and the non-virulent influenza virus preparation is present in an amount of about 1 to about 100 μg, preferably about 10 to about 75 μg.

The fusion (F) protein may comprise multimeric fusion (F) proteins, which may include, when analyzed under non-reducing conditions, heterodimers of molecular weight approximately 70 kDa and dimeric and trimeric forms.

The attachment (G) protein may comprise, when analyzed under non-reducing conditions, oligomeric G protein, G protein of molecular weight approximately 95 kDa and G protein of molecular weight approximately 55 kDa.

The matrix (M) protein may comprise, when analyzed under non-reducing conditions, protein of molecular weight approximately 28 to 34 kDa.

The RSV protein mixture employed herein, when analyzed by reduced SDS-PAGE analysis, may comprise the fusion (F) protein comprising an $F_1$ subunit of molecular weight approximately 48 kDa and an $F_2$ subunit of about 23 kDa, the attachment (G) protein comprising a G protein of molecular weight approximately 95 kDa and a G protein of molecular weight approximately 55 kDa, and the matrix (M) protein comprising an M protein of approximately 31 kDa.

The RSV protein mixture employed in the invention may comprise the F, G and M proteins in the relative proportions of:

F about 35 to about 70 wt %

G about 5 to about 30 wt %

M about 10 to about 50 wt %

When analyzed by SDS-PAGE under reducing conditions and densitometric scanning following silver staining, the ratio of $F_1$ subunit of molecular weight approximately 48 kDa to $F_2$ subunit of molecular weight approximately 23 kDa in is this mixture may be approximately between 1:1 and 2:1. The mixture of F, G and M proteins may have a purity of at least about 75%, preferably at least about 85%.

The mixture employed herein in accordance with this aspect of the invention, having regard to the method of isolation employed herein as described below, is devoid of monoclonal antibodies and devoid of lentil lectin and concanavalin A.

The RSV proteins provided in the mixture of proteins employed herein generally are substantially non-denatured by the mild conditions of preparation and may comprise RSV proteins from one or both of subtypes RSV A and RSV B.

The composition and manner of preparation of the mixture of RSV proteins is fully described in U.S. patent application Ser. No. 08/679,060, filed Jul. 12, 1996, and in published PCT Application WO 98/02457, the disclosures of which are incorporated herein by reference. As described therein, the mixture of RSV proteins may be obtained by coisolating and copurifying the mixture from the virus. RSV cells are grown in a cell culture and separated from the cell culture. The F, G and M proteins are solubilized from the separated virus and the solubilized RSV protein are coisolated and copurified. Such coisolation and copurification may be effected by loading the solubilized proteins onto an ion-exchange matrix, preferably a calcium phosphate matrix, specifically a hydroxyapatite matrix, and selectively eluting the F, G and M proteins from the ion-exchange matrix. The grown virus may first be washed with urea to remove contaminants without substantially removing F, G and M proteins.

The non-virulent influenza preparation employed herein usually comprises a plurality of different non-virulent influenza virus strains, including attenuated viruses, which may be cold adapted. Conventionally influenza virus vaccines are formulated annually based on the strains prevalent and extant during the provisions flu season and may comprise two, three or more different strains. Such influenza virus preparation may be rendered non-virulent in any convenient manner, such as by inactivation with any convenient inactivating agent, such as formaldehyde. The non-virulent influenza preparation may comprise influenza antigens, such as HA, NA, NP, M, PB1, NS1, NS2 or PB2, which may be isolated from attenuated or inactivated virus or may be prepared recombinantly.

In a further aspect of the present invention, there is provided a method of immunizing a human host against disease caused by infection by respiratory syncytial virus (RSV) and influenza virus, which comprises administering to the host an immunoeffective amount of the immunogenic composition provided herein.

The immunogenic composition preferably is formulated as a vaccine for in vivo administration to the host wherein the individual components (a) and (b) of the composition are formulated such that the immunogenicity of the individual components (a) and (b) is not impaired. The formulation provided herein enables the elderly to be protected by such immunization.

The present invention provides, in an additional aspect thereof, a method of producing a vaccine for protection against disease caused by respiratory syncytial virus (RSV) infection and by influenza virus infection, comprising administering the immunogenic composition provided herein to a test host to determine the amount of and frequency of administration thereof to confer protection against disease caused by RSV and by influenza virus; and formulating the immunogenic composition in a form suitable for administration to a treated host in accordance with the determined amount and frequency of administration. The treated host may be a human.

The present invention further extends to the immunogenic composition of the invention when used as a vaccine. In addition, the present invention includes the use of (a) a mixture of purified fusion (F) protein, attachment (G) protein and matrix (M) protein of RSV and (b) a non-virulent influenza virus preparation in the manufacture of a vaccine for conferring protection in a host against disease caused by RSV and by influenza virus.

Advantages of the present invention include the provision of a single vaccine formulation which permits immunization of the elderly against disease caused by infection by RSV and influenza virus in a single immunization regimen.

BRIEF DESCRIPTION OF DRAWINGS

In each of the Figures, a common legend is used for identification of the immunogens used in the experiments for which the data is presented in the Figures is as follows.

(a) phosphate buffered saline (PBS); (b) 200 µg PCPP adjuvant; (c) $1.5 \times 10^6$ pfu live RSV; (d) 200 to 400 HA units live influenza; (e) 5 µg Fluzone® vaccine with PCPP adjuvant; (f) 1 µg RSV vaccine with PCPP adjuvant; (g) 5 µg Fluzone® vaccine plus 1 µg RSV vaccine with PCPP adjuvant; (h) 5 µg Fluzone® vaccine plus 1 µg RSV vaccine with no adjuvant; (i) 5 µg Fluzone® vaccine with no adjuvant; (j) 1 µg RSV vaccine with no adjuvant.

GENERAL DESCRIPTION OF INVENTION

The mixture of F, G and M proteins of RSV used herein may be coisolated and copurified from RS virus. As described in the aforesaid U.S. Ser. No. 08/679,060 and WO 98/02457, the virus is grown on a vaccine quality cell line, such as VERO cells and human diploid cells, such as MRC5 and WI38, and the grown virus is harvested. The fermentation may be effected in the presence of fetal bovine serum (FBS) and trypsin.

The viral harvest is filtered and then concentrated, typically using tangential flow ultrafiltration with a membrane of desired molecular weight cut-off, and diafiltered. The virus harvest concentrate may be centrifuged and the supernatant discarded. The pellet following centrifugation may first be washed with a buffer containing urea to remove soluble contaminants while leaving the F, G and M proteins substantially unaffected, and then recentrifuged. The pellet from the centrifugation then is detergent extracted to solubilize the F, G and M proteins from the pellet. Such detergent extraction may be effected by resuspending the pellet to the original harvest concentrate volume in an extraction buffer containing a detergent, such as a non-ionic detergent, including TRITON® X-100, a non-ionic detergent which is octadienyl phenol (ethylene glycol)$_{10}$. Other detergents which may be used include octylglucoside and Mega detergents.

Following centrifugation to remove non-soluble proteins, the F, G and M protein extract is purified by chromatographic procedures. The extract may first be applied to an ion exchange chromatography matrix to permit binding of the F, G and M proteins to the matrix while impurities are permitted to flow through the column. The ion-exchange chromatography matrix may be any desired chromatography material, particularly a calcium phosphate matrix, specifically hydroxyapatite, although other materials, such as DEAE and TMAE and others, may be used.

The bound F, G and M proteins then are coeluted from the column by a suitable eluant. The resulting copurified F, G and M proteins may be further processed to increase the purity thereof.

The purified F, G and M proteins employed herein may be in the form of homo and hetero oligomers including F:G heterodimers and including dimers, tetramers and higher species. The RSV protein preparations prepared following this procedure demonstrated no evidence of any adventitious agent, hemadsorbing agent or live virus.

The influenza virus vaccine utilized herein is a sterile suspension prepared from influenza virus propagated in chicken embryos. The virus-containing allantoic fluids are harvested and inactivated with formaldehyde. The virus is then concentrated and purified in a linear sucrose density gradient solution, using a continuous flow centrifuge. The virus is then chemically disrupted using Triton® X-100 producing a split-antigen. The split-antigen is then further purified by chemical means and suspended in sodium phosphate-buffered isotonic sodium chloride solution. Gelatin (0.05%) is then added as a stabilizer and thimerosol (1:10,000) is added as a preservative.

The commercial split flu antigen vaccine (Fluzone®) as used herein and prepared following the above procedure was obtained from Connaught Laboratories Inc., Swiftwater, Pa., USA.

As set forth in detail in the Examples below, various combinations of RSV-A subunit vaccine and trivalent influenza vaccine were prepared with or without PCPP adjuvant and were tested for their immunogenicity in comparison to several controls. In the immunization studies, details of which are provided below, Balb/c mice were immunized with two injections of immunogen given three weeks apart. Bleeds were collected to monitor the immune response and, at the end of the study, the mice were challenged with either influenza or RSV to determine whether protection was obtained.

Details of the results obtained are set forth in the Examples below and in FIGS. 1 to 9. It was found that neither the RSV nor influenza antigen interfered or impaired the immunogenicity of the other, both in adjuvanted and unadjuvanted form. In addition, when adjuvanted, the combination of the RSV and influenza immunogen produced an enhanced immune response to RSV in comparison to the absence of the influenza immunogens.

It is clearly apparent to one skilled in the art, that the various embodiments of the present invention have many applications in the fields of vaccination, diagnosis and treatment of respiratory syncytial virus and influenza virus infections, and the generation of immunological agents. A further non-limiting discussion of such issue is further presented below.

1. Vaccine Preparation and Use

Immunogenic compositions, suitable to be used as vaccines, may be prepared from mixtures comprising immunogenic F, G and M proteins of RSV along with a non-virulent influenza virus preparation. The immunogenic composition elicits an immune response which produces antibodies, including anti-RSV antibodies including anti-F, anti-G and anti-M antibodies as well as anti-influenza antibodies to each of the strains present in the formulation. Such antibodies may be viral neutralizing and/or anti-fusion antibodies.

Immunogenic compositions including vaccines may be prepared as injectables, as liquid solutions, suspensions or emulsions. The active immunogenic ingredients may be mixed with pharmaceutically acceptable excipients which are compatible therewith. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by subcutaneous, intradermal or intramuscular injection. Alternatively, the immunogenic compositions formulated according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Such suppositories may be formed from mixtures containing the active immunogenic ingredient(s) in the range of about 0.5 to about 10%, preferably about 1 to 2%. Oral formulations may include normally employed carriers such as, pharmaceutical grades of saccharine, cellulose and magnesium carbonate. These compositions can take the form of solutions, suspensions, tablets, pills, capsules, sustained release formulations or powders and contain about 1 to 95% of the active ingredients, preferably about 20 to about 75%.

The immunogenic preparations and vaccines are administered in a manner compatible with the dosage formulation, and in such amount as will be therapeutically effective, immunogenic and protective. The quantity to be administered depends on the subject to be treated, including, for example, the capacity of the individual's immune system to synthesize antibodies, and, if needed, to produce a cell-mediated immune response. Precise amounts of active ingredients required to be administered depend on the judgment of the practitioner. However, suitable dosage ranges are readily determinable by one skilled in the art and may be of the order of micrograms to milligrams of the active ingredient(s) per vaccination. Suitable regimes for initial administration and booster doses are also variable, but may include an initial administration followed by subsequent booster administrations. The dosage may also depend on the route of administration and will vary according to the size of the host.

The concentration of the active ingredients in an immunogenic composition according to the invention is in general about 1 to 95%. A vaccine which contains antigenic material of only one pathogen is a monovalent vaccine.

Immunogenicity can be significantly improved if the antigens are co-administered with adjuvants. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established. While the usefulness of alum is well established for some applications, it has limitations. For example, alum is ineffective for influenza vaccination and usually does not elicit a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's incomplete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Methods of determining tissue culture infectious dose$_{50}$ (TCID$_{50}$/mL), plaque and neutralization titres, not explicitly described in this disclosure are amply reported in the scientific literature and well within the scope of those skilled in the art. Protein concentrations were determined by the bicinchoninic acid (BCA) method as described in the Pierce Manual (23220, 23225; Pierce Chemical company, U.S.A.), incorporated herein by reference.

CMRL 1969 and Iscove's Modified Dulbecco's Medium (IMDM) culture media were used for cell culture and virus growth. The cells used in this study are vaccine quality African green monkey kidney cells (VERO lot M6) obtained from Institut Mérieux. The RS viruses used were the RS virus subtype A (Long and A2 strains) obtained from the American Type culture Collection (ATCC), a recent subtype A clinical isolate and RSV subtype B clinical isolate from Baylor College of Medicine.

Example 1

This Example illustrates the production of RSV on a mammalian cell line on microcarrier beads in a 150 L controlled fermenter.

Vaccine quality African green monkey kidney cells (VERO) at a concentration of $10^5$ cells/mL were added to 60 L of CMRL 1969 medium, pH 7.2 in a 150 L bioreactor containing 360 g of Cytodex-1 microcarrier beads and stirred for 2 hours. An additional 60 L of CMRL 1969 was added to give a total volume of 120 L. Fetal bovine serum was added to achieve a final concentration of 3.5%. Glucose was added to a final concentration of 3 g/L and L-glutamine was added to a final concentration of 0.6 g/L. Dissolved oxygen (40%), pH (7.2), agitation (36 rpm) and temperature (37° C.) were controlled. Cell growth, glucose, lactate and glutamine levels were monitored. At day 4, the culture medium was drained from the fermenter and 100 L of E199 media (no fetal bovine serum) was added and stirred for 10 minutes. The fermentor was drained and filled again with 120 L of E199 media.

An RSV inoculum of RSV subtype A was added at a multiplicity of infection (M.O.I.) of 0.001 and the culture was then maintained for 3 days before one-third to one-half of the medium was drained and replaced with fresh medium. On day 6 post-infection, the stirring was stopped and the beads allowed to settle. The viral culture fluid was drained and filtered through a 20 mm filter followed by a 3 mm filter prior to further processing.

The clarified viral harvest was concentrated 75- to 150-fold using tangential flow ultrafiltration with 300 NMWL membranes and diafiltered with phosphate buffered saline containing 10% glycerol. The viral concentrate was stored frozen at −70° C. prior to further purification.

Example 2

This Example illustrates the process of purifying RSV subunits from a viral concentrate of RSV subtype A.

A solution of 50% polyethylene glycol-8000 was added to an aliquot of virus concentrate prepared as described in Example 1 to give a final concentration of 6%. After stirring at room temperature for one hour, the mixture was centrifuged at 15,000 RPM for 30 min in a Sorvall SS-34 rotor at 4° C. The viral pellet was suspended in 1 mM sodium phosphate, pH 6.8, 2 M urea, 0.15 M NaCl, stirred for 1 hour at room temperature, and then recentrifuged at 15,000 RPM for 30 min. in a Sorvall SS-34 rotor at 4° C. The viral pellet was then suspended in 1 mM sodium phosphate, pH 6.8, 50 mM NaCl, 1% Triton X-100 and stirred for 30 minutes at room temperature. The insoluble virus core was removed by centrifugation at 15,000 RPM for 30 min. in a Sorval SS-34 rotor at 4° C. The soluble protein supernatant was applied to a column of ceramic hydroxyapatite (type II, Bio-Rad Laboratories) and the column was then washed with five column volumes of 1 mM sodium phosphate, pH 6.8, 50 mM NaCl, 0.02% Triton X-100. The RSV subunit composition from RSV subtype A, containing the F, G and M proteins, was obtained by eluting the column with 10 column volumes of 1 mM sodium phosphate, pH 6.8, 400 mM NaCl, 0.02% Triton X-100.

Example 3

This Example illustrates the production of influenza virus.

The influenza virus vaccine utilized herein is a sterile suspension prepared from influenza virus propagated in chicken embryos. The virus containing allantoic fluids are harvested and inactivated with formaldehyde. The virus is then concentrated and purified in a linear sucrose density gradient solution, using a continuous flow centrifuge. The virus is then chemically disrupted using Triton® X-100 producing a split-antigen. The split-antigen is then further purified by chemical means and suspended in sodium phosphate-buffered isotonic sodium chloride solution. Gelatin (0.05%) is then added as a stabilizer and thimerosol (1:10,000) is added as a preservative.

The commercial vaccine (Fluzone®) as used herein, prepared as described above was obtained from Connaught Laboratories Inc., Swiftwater, Pa., USA.

Example 4

This Example illustrates the immunization protocol used in the mice studies.

Mice were bled one day prior to the first immunization and also on days 22 and 28 of the study. Immunizations were done on days 1 and 22. Both immunizations were administered intramuscularly in the thigh muscle. Each immunization was done at two injection sites (both right and left thigh muscles; 0.05 ml/site). The dose of RSV vaccine was 1 μg total protein and the dose of Fluzone® (split flu antigen) vaccine was 5 μg total protein per dose. The RSV or Fluzone® (split flu antigen) vaccines were administered in the presence or absence of adjuvant. The adjuvant used was poly-di(carboxylatophenoxy)-phosphazene (PCPP) given at 200 μg/dose. Mice that received live RSV (A2 strain) as the immunogen were given $1.5 \times 10^6$ pfu/dose intranasally. Mice that received live influenza virus (A/Taiwan Strain) as the immunogen were given 200 to 400 HAU/dose intraperitonally. Virus challenge with either RSV or influenza was administered intranasally on day 29 using the same dose as given for the live virus immunized mice. All animals were sacrificed on day 33. Lungs were removed and frozen immediately in liquid nitrogen for later determination of virus titre.

Example 5

This Example illustrates the determination of RSV titres in the lungs of mice.

Mouse lungs were removed at the time of sacrifice, quick frozen in liquid nitrogen, and then stored at −70° C. until assayed for virus titre. To process the lungs, they were thawed, weighed and then homogenized in Dulbecco's Modified Eagles (DME) tissue culture media containing 10% fetal bovine serum. The homogenate was centrifuged at 200×g for 15 min to remove cell debris and the supernatant was collected. The supernatant was assayed for RSV titres using the RSV plaque assay, as described in Example 6.

When the mice were challenged with RSV, FIG. 3, again a good immune response was observed in the combination and adjuvant (lane g) showing very low titres in the lungs, comparable to the RSV alone (lane f) or the live RSV (lane c). This also shows the lack of interference between the influenza component and the RSV components.

Example 6

This Example describes the RSV plaque assay.

Vero cells were grown in CMRL 1969 media plus 10% FBS for RSV titrations. Test samples were diluted serially in 10-fold steps and added to 24-well plates containing confluent Vero cells for 1 to 2 hours. Following adsorption, the sample was removed and replaced with media containing 0.75% methyl cellulose. After 4 to 5 days incubation, virus plaques were detected by probing the wells with monoclonal anti-F antibody. Bound antibody was visualized using sequential incubation with horse radish peroxidase-conjugated donkey anti-mouse immunoglobulin and 4-choro-1-napthol/$H_2O_2$. Plaques were scored manually.

Example 7

This Example describes the RSV plaque reduction assay.

Test sera were heat-inactivated at 56° C. for 30 minutes. Samples were diluted in four-fold serial steps and mixed with an equal volume of RSV A (long strain; 30–70 PFU) in assay media containing 10% guinea pig complement. After one hour incubation at 37° C. the mixture was inoculated onto Vero cells for 1 to 2 hours. This was followed by an overlay with 0.75% methyl cellulose and incubation for 4 to 5 days. Virus plaques were detected as described for the RSV plaque assay in Example 6. The neutralization titre is expressed as the reciprocal of the dilution which results in 60% reduction in plaque formation (as determined by linear interpolation analysis).

Figure 2:
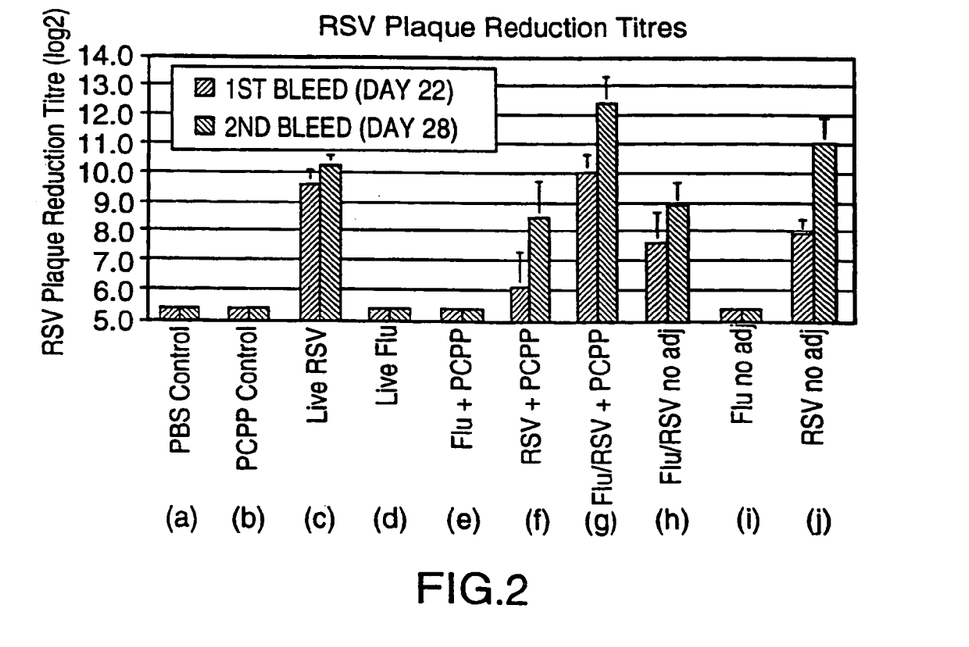
FIG. 2 shows the RSV plaque reduction titres in mice immunized with each of the immunogens.
Figure 3:
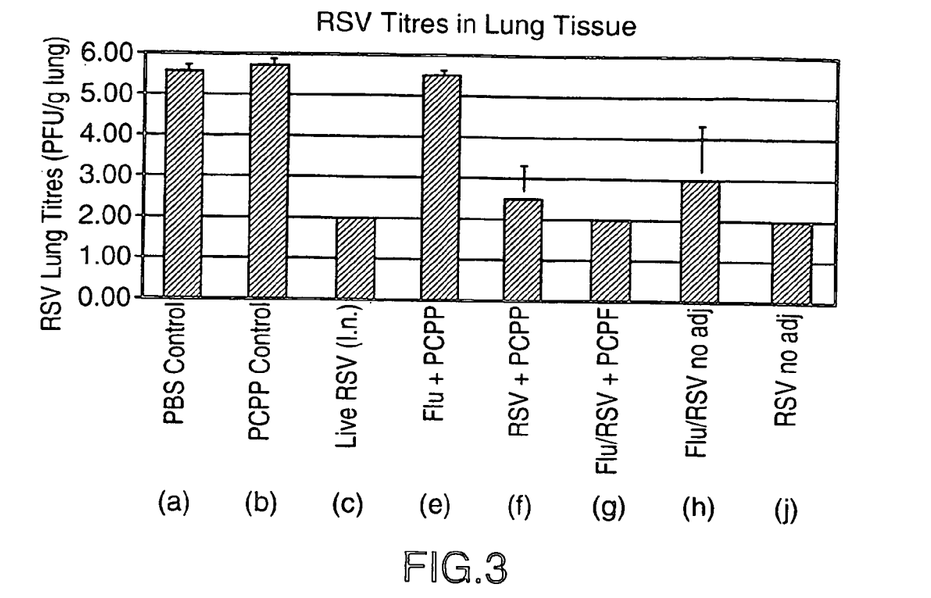
FIG. 3 shows the RSV titres in the lungs of mice immunized with each of the immunogens and then challenged with live RSV.

The enhancement of the RSV response is illustrated in FIG. 2 where plaque reduction titres were looked at. The RSV/Flu combination (lane g) again shows a higher titre than the RSV alone (lane f).

Example 8

This Example describes the mouse anti-RSV F antibody ELISA.

Anti-F immunoglobulin antibody titres in mouse sera were measured in an antigen-specific ELISA employing native F protein as the solid-phase coat. The F protein was purified by immunoaffinity chromatography using an immobilized anti-F monoclonal antibody. Wells were coated with F protein, then blocked with 1% BSA in PBS. Dilutions of test serum samples were added, and after incubation, the wells were washed again with 1% BSA. The bound F-specific antibodies were detected with horse radish peroxidase-labeled antibody specific for mouse IgG (H+L chains), followed after further washing by tetramethylbenzidine plus hydrogen peroxide substrate. Colour formation was measured at 450 nm in an automatic plate reader. The antibody titre is expressed as the reciprocal of the greatest four-fold dilution at which optical density remains double that of a negative control.

Figure 1:
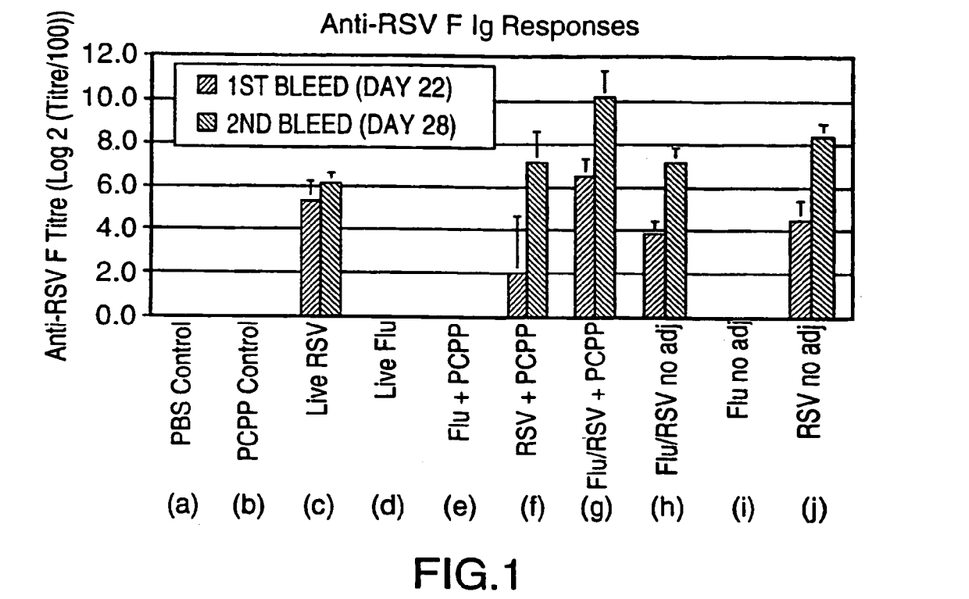
FIG. 1 shows the anti-RSV F immunoglobulin titres in mice immunized with each of the immunogens.

As can be seen from FIG. 1, RSV-F IgG antibody response was observed in the RSV/Flu immunizations (lanes g+h), either with or without adjuvant. These results are comparable to RSV immunization alone (lane f) and in fact the combination immunization (lane g) shows an enhanced RSV response over RSV alone (lane f). This shows that there was no interference between the influenza component and the RSV components.

Example 9

This Example describes the mouse anti-influenza antibody ELISA.

Influenza strain-specific antibody titres in mouse sera were measured using microitre plates coated with the appropriate influenza strain (A/Texas, A/Johannesburg, or B/Harbin). Plate processing and development was done as described for the RSV-F antibody ELISA in Example 8.

Figure 4:
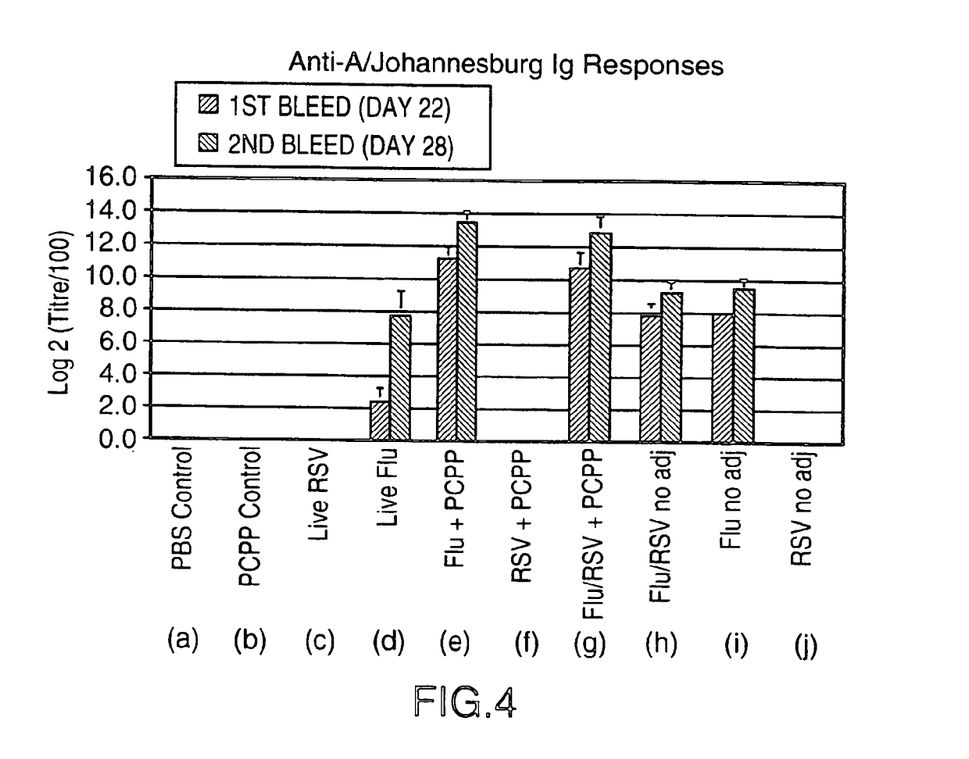
FIG. 4 shows the anti-A/Johannesburg influenza immunoglobulin titres in mice immunized with each of the immunogens.
Figure 5:
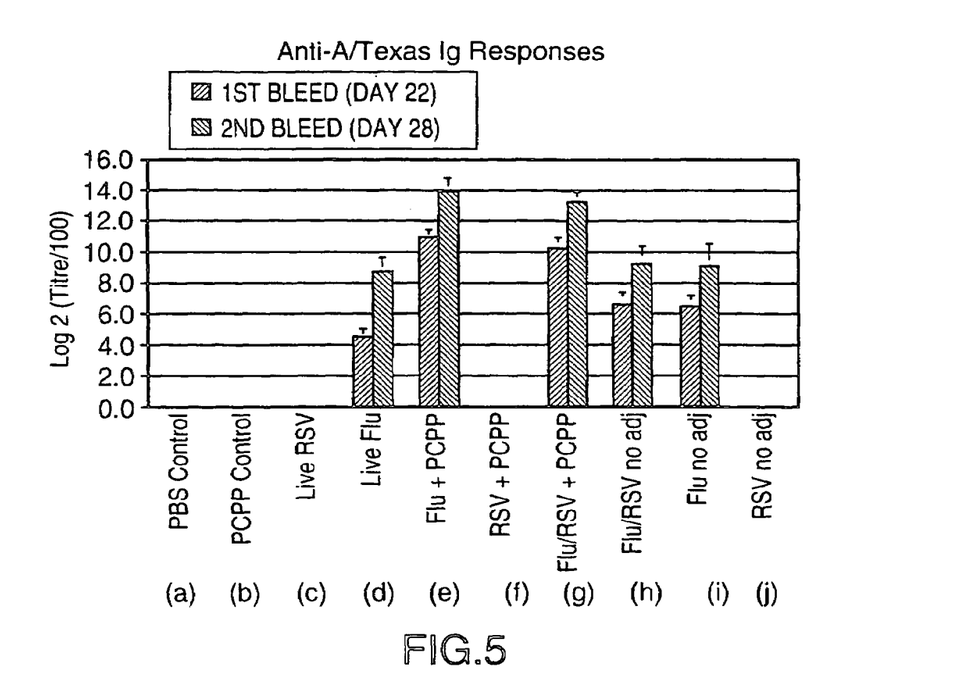
FIG. 5 shows the anti-A/Texas influenza immunoglobulin titres in mice immunized with each of the immunogens.
Figure 6:
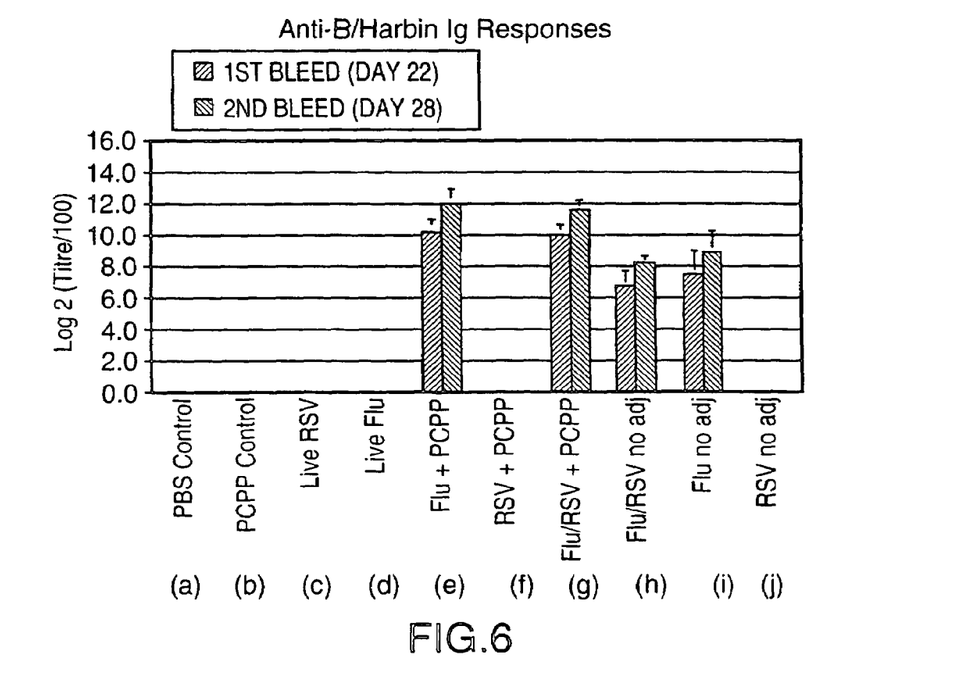
FIG. 6 shows the anti-B/Harbin influenza immunoglobulin titres in mice immunized with each of the immunogens.

As can be seen from FIGS. 4, 5, 6, all three strains of influenzae elicited a good antibody response to influenza virus in the combination RSV/Flu administration (lane g). This was comparable to the flu vaccine administered alone (lane e). This again shows that the combination vaccine did not reduce or interfere with the immune response to the influenza component.

Example 10

This Example describes the influenza hemagglutination inhibition assay.

Sera samples were heated at 56° C. for 30 minutes to inactivate complement 1 and then treated with trypsin and potassium periodate to destroy endogenous inhibitors of hemagglutination. Serially diluted antisera were tested for their ability is to inhibit the agglutination of chicken red blood cells by four HA units of influenza virus (A/Texas, A/Johannesburg, or B/Harbin) in a standard hemagglutination inhibition assay.

Figure 7:
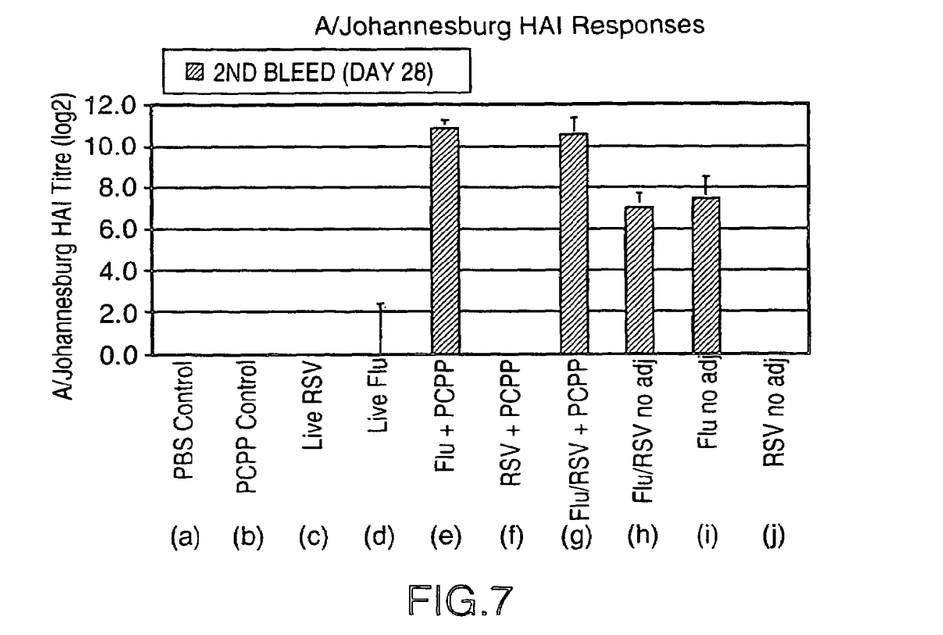
FIG. 7 shows the anti-A/Johannesburg influenza hemagglutination inhibition titres in mice immunized with each of the immunogens.
Figure 8:
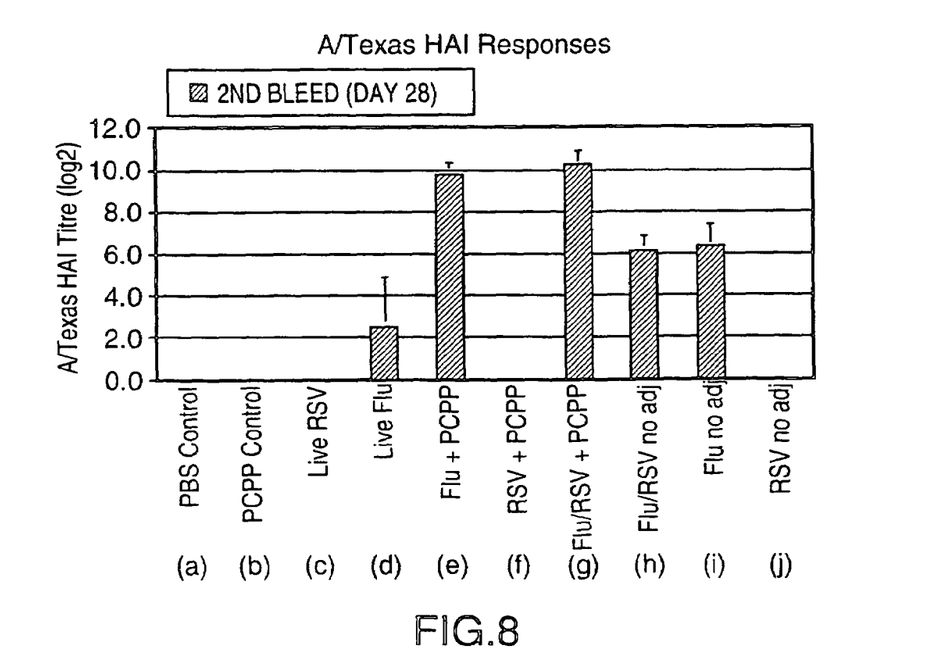
FIG. 8 shows the anti-A/Texas influenza hemagglutination inhibition titres in mice immunized with each of the immunogens.
Figure 9:
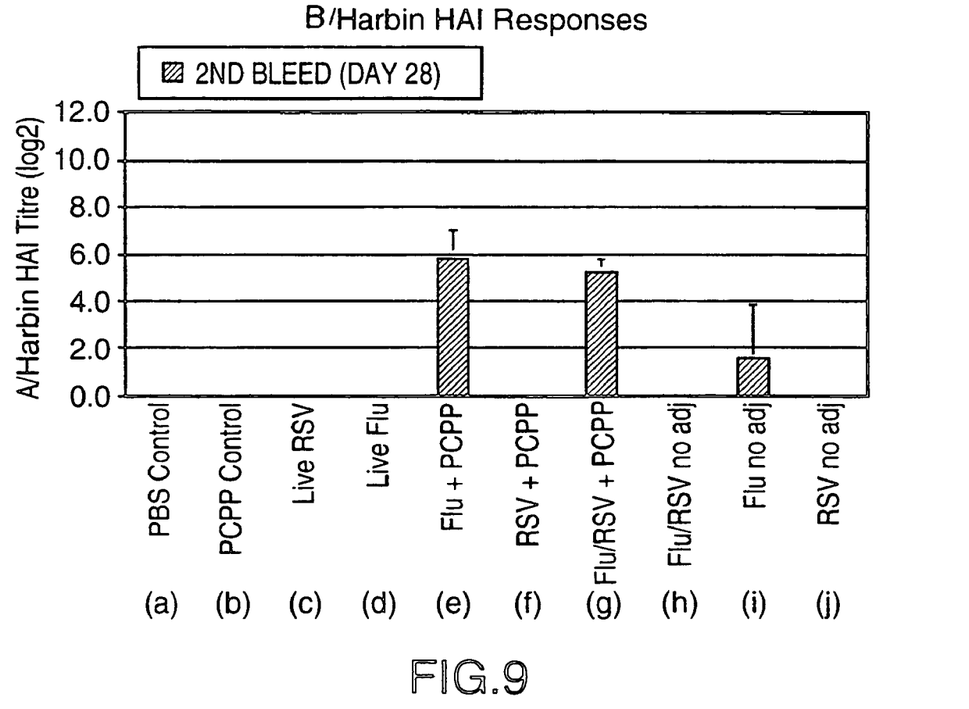
FIG. 9 shows the anti-B/Harbin influenza hemagglutination inhibition titres in mice immunized with each of the immunogens.

FIGS. 7, 8 and 9 shows that the combination vaccine (lane g) produced as good haemagglutinin (HA) titres as the Flu vaccine as its own. Again this illustrates that the RSV component did not interfere with the eliciting of a good influenza immune response, in this case as measured by HAI.

SUMMARY OF THE DISCLOSURE

In summary of the disclosure, the present invention provides a multivalent immunogenic composition comprising an RSV protein subunit component and a non-virulent influenza virus preparation wherein the active ingredients do not interfere with the immunogenicity of the other and which is suitable for administration to adults and the elderly. Modifications are possible with the scope of the invention.

REFERENCES

1. Glezen, W. P., Paredes, A. Allison, J. E., Taber, L. H. and Frank, A. L. (1981). J. Pediatr. 98, 708–715.
2. Chanock, R. M., Parrot, R. H., Connors, M., Collins, P. L. and Murphy, B. R. (1992) Pediatrics 90, 137–142.
3. Martin, A. J. Gardiner, P. S. and McQuillin, J. (1978). Lancel ii, 1035–1038.
4. Robbins, A., and Freeman, P. (1988) Sci. Am. 259, 126–133.
5. Glezen, W. P., Taber, L. H., Frank, A. L. and Kasel, J. A. (1986) Am. J. Dis. Child. 140, 143–146.
6. Katz, S. L. New vaccine development establishing priorities. Vol. 1. Washington: National Academic Press. (1985) pp. 397–409.
7. Wertz, G. W., Sullender, W. M. (1992) Biotech. 20, 151–176.
8. McIntosh, K. and Chanock, R. M. (1990) in Fields Virology (Fields, B. M., and Knipe, D. M. eds.) pp. 1045–1075, Raven Press, Ltd., New York.
9. Murry A R, Dowell S F, 1997. Respiratory syncytial virus: not just for kids. Hosp. Pract. (Off Ed) 1997 Jul. 15; 32(7): 87–8, 91–4.
10. Mlinaric-Galinovic G, Falsey A R, Walsh E E, 1996. Respiratory syncytial virus infection in the elderly. Eur J Clin Microbiol Infect Dis 1996.
11. Collins, P., McIntosh, K., and Chanock, R. M. in "Fields Virology" ed. by Fields, B. N., Knipe, D. M., and Howley, P. M., Lippincott-Raven Press, New York, (1996) pp. 1313–1351.
12. Walsh, E. E., Hall, C. B., Briselli, M., Brandiss, M. W. and Schlesinger, J. J. (1987) J. Infect. Dis. 155, 1198–1204.
13. Walsh, E. E., Hruska, J. (1983) J. Virol. 47, 171–177.
14. Levine, S., Kleiber-France, R., and Paradiso, P. R. (1987) J. Gen. Virol. 69, 2521–2524.
15. Anderson, L. J. Hierholzer, J. C., Tsou, C., Hendry, R. M., Fernie, B. F., Stone, Y. and McIntosh, K. (1985), J. Infect. Dis. 151, 626–633.
16. Johnson, P. R., Olmsted, R. A., Prince, G. A., Murphy, B. R., Alling, D. W., Walsh, E. E. and Collins, P. L. (1987) J. Virol. 61 (10), 3163–3166.
17. Cherrie, A. H., Anderson, K., Wertz, G. W., and Openshaw, P. J. M. (1992) J. Virology 66, 2102–2110.
18. Kim, H. W., Canchola, J. G., Brandt, C. D., Pyles, G., Chanock, R. M. Jensen, K., and Parrott, R. H. (1969) Amer. J. Epidemiology 89, 422–434.
19. Firedewald, W. T., Forsyth, B. R., Smith, C. B., Gharpure, M. S., and Chanock, R. M. (1968) JAMA 204, 690–694.
20. Walsh, E. E., Brandriss, M. W., Schlesinger, J. J. (1985) J. Gen. Virol. 66, 409–415.
21. Walsh, E. E., Schlesinger, J. J. and Brandriss, M. W. (1984) J. Gen. Virol. 65, 761–766.
22. Routledge, E. G., Willcocks, M. M., Samson, A. C. R., Morgan, L., Scott, R., Anderson, J. J., and Toms, G. L. (1988) J. Gen. Virology 69, 293–303.
23. Fulginiti, V. A., Eller, J. J., Sieber, O. F., Joyner, I. W., Minamitani, M. and Meiklejohn, G. (1969) Am J. Epidemiol. 89 (4), 435–448.
24. Chin, J., Magoffin, R. L., Shearer, L. A., Schieble, J. H. and Lennette, E. H. (1969) Am. J. Epidemiol. 89 (4), 449–463.
25. Kapikian, A. Z., Mitchell, R. H., Chanock, R. M., Shvedoff, R. A. and Stewart, C. E. (1969) Am. J. Epidemiol. 89 (4), 405–421.
26. Kim, H. W., Arrobio, J. O., Pyles, G., Brandt, C. D. Camargo, E., Chanock, R. M. and Parrott, R. H. (1971) Pediatrics 48, 745–755.
27. Wright, P. F., Belshe, R. B., Kim, H. W., Van Voris, L. P. and Chanock, r. M. (1982) Infect. Immun. 37 (1), 397–400.
28. Wright, P. F., Chinozaki, T. and Fleet, W. (1976) J. Pediatr. 88, 931–936.
29. Belshe, R. B., Van Voris, P. and Mufson, M. A. (1982) J. Infect. Dis. 145, 311–319.
30. Murphy, B. R., Prince, G. A., Walsh, E. E., Kim, H. W., Parrott, R. H., Hemming V. G., Rodriguez, W. J., and Chanock, R. M. J. Clin. Microbiol. (1986), 24(2), 197–202.

31. Connors, M., Collins, P. L., Firestone, C. Y., Sotnikov, A. V., Waitze, A., Davis, A. R., Hung, P. P., Chanock, R. M., Murphy, b. (1992) Vaccine, 10, 475–484.
32. Prince, G. A., Jenson, A. B., Hemming, V. G., Murphy, E. R., Walsh, E. E., Horswood, R. L. and Chanock, R. L. (1986b) J. Virol. 57 (3), 721–728.
33. Piedra, P. A., Camussi, F. and Ogra, P. L. (1989) J. Gen. Virol. 70,325–333.
34. Walsh, E. E., Hall, C. B., Briselli, M., Brandiss, M. W. and Schlesinger, J. J. (1987) J. Infect. Dis. 155 (6), 1198–1204.

We claim:

1. A multi-valent immunogenic composition, which comprises:
    (a) a mixture of purified fusion (F), attachment (G) and matrix (M) protein of RSV,
    (b) a non-virulent influenza virus preparation, and
    (c) an adjuvant,
    said immunogenic composition being formulated for in vivo administration to the host wherein the individual components (a) and (b) of the composition are formulated such that the immunogenicity of the individual components (a) and (b) is not impaired,
    wherein said adjuvant is poly-di(carboxylatophenoxy)-phosphazene (PCPP) and is present in an amount which imparts an enhanced immune response to RSV when compared to the mixture (a) formulated with the adjuvant in the absence of the non-virulent virus preparation, and
    wherein said non-virulent influenza virus preparation is prepared as follows:
    (i) preparing a sterile suspension of influenza virus propagated in chicken embryos;
    (ii) inactivating the virus in the suspension with formaldehyde;
    (iii) concentrating and purifying the virus in a linear sucrose density gradient solution, where said concentrating and purifying is performed using a continuous flow centrifuge;
    (iv) chemically disrupting the purified inactivated virus using Triton X-100, resulting in a split-antigen;
    (v) further purifying the split-antigen by chemical means;
    (vi) suspending the purified split-antigen in a sodium phosphate-buffered isotonic sodium chloride solution; and
    (vii) adding to the split-antigen solution a 0.05% Gelatin stabilizer and the preservative thimerosol at a 1:10,000 concentration.

2. The immunogenic composition of claim 1 wherein said mixture (a) is present in an amount of about 10 to about 200 μg and (b) is present in an amount of about 1 to about 100 μg, in a single dose.

3. The immunogenic composition of claim 1 wherein said fusion (F) protein comprises multimeric fusion (F) proteins.

4. The immunogenic composition of claim 3 wherein, when analyzed under non-reducing conditions, said multimeric fusion (F) protein includes heterodimers of molecular weight approximately 70 kDa and dimeric and trimeric forms.

5. The immunogenic composition of claim 1 wherein, when analyzed under non-reducing conditions, said attachment (G) protein comprises G protein of molecular weight approximately 95 kDa and G protein of molecular weight approximately 55 kDa and oligomeric G protein.

6. The immunogenic composition of claim 1 wherein, when analyzed by SDS-PAGE under non-reducing conditions, said matrix (M) protein comprises M protein of molecular weight approximately 28 to 34 kDa.

7. The immunogenic composition of claim 1 wherein, when analyzed by reduced SDS-PAGE analysis, said fusion (F) protein comprises an $F_1$ subunit of molecular weight approximately 48 kDa and an $F_2$ subunit of molecular weight approximately 23 kDa, said attachment (G) protein comprises a G protein of molecular weight approximately 95 kDa and a G protein of molecular weight approximately 55 kDa, and said matrix (M) protein comprises an M protein of approximately 31 kDa.

8. The immunogenic composition of claim 1 wherein said F, G and M proteins are present in mixture (a) in the relative proportions of:
    F from about 35 to about 70 wt %
    G from about 5 to about 30 wt %
    M from about 10 to about 50 wt %.

9. The immunogenic composition of claim 8 wherein, when analyzed by SDS-PAGE under reducing conditions and silver stained, the ratio of $F_1$ subunit of molecular weight approximately 48 kDa to $F_2$ subunit of molecular weight approximately 23 kDa is between 1:1 to about 2:1 as determined by scanning densitometry.

10. The immunogenic composition of claim 9 wherein said mixture is at least about 75% pure.

11. The immunogenic composition of claim 1 wherein said RSV proteins in said mixture are from one or both of subtypes RSV A and RSV B.

12. A method of inducing an immune response in a human host, which comprises administering to the host the immunogenic composition of claim 1.

13. The method of claim 12 wherein said host is a human host of at least 18 years of age.

* * * * *